United States Patent
Schubert et al.

(10) Patent No.: US 7,053,229 B2
(45) Date of Patent: May 30, 2006

(54) PROCESS FOR THE PRODUCTION OF 4-(17α-ALKOXYMETHYL-17β-SUBSTITUTED 3-OXOESTRA-4,9-DIEN-11β-YL)BENZALDEHYDE-(1E)-OXIME DERIVATIVES

(75) Inventors: Gerd Schubert, Jena (DE); Sven Ring, Jena (DE)

(73) Assignee: Schering AG, Berlin (DE)

( * ) Notice: Subject to any disclaimer, the term of this patent is extended or adjusted under 35 U.S.C. 154(b) by 246 days.

(21) Appl. No.: 10/416,028

(22) PCT Filed: Nov. 9, 2001

(86) PCT No.: PCT/DE01/04219

§ 371 (c)(1),
(2), (4) Date: Oct. 20, 2003

(87) PCT Pub. No.: WO02/38583

PCT Pub. Date: May 16, 2002

(65) Prior Publication Data

US 2004/0059141 A1    Mar. 25, 2004

(30) Foreign Application Priority Data

Nov. 10, 2000 (DE) ................. 100 56 677

(51) Int. Cl.
*C07J 1/00* (2006.01)
*C07D 315/00* (2006.01)
*C07C 251/32* (2006.01)

(52) U.S. Cl. ............... 552/648; 549/424; 564/254; 564/255

(58) Field of Classification Search ......... 552/648; 549/424; 546/254, 255
See application file for complete search history.

(56) References Cited

FOREIGN PATENT DOCUMENTS

| DE | 61 263 A | 12/1968 |
|---|---|---|
| DE | 16 18 340 A | 3/1971 |
| EP | 0 648 779 A2 | 4/1995 |

OTHER PUBLICATIONS

A. Jumar et al., "Uber die Herstellung und Reaktionsfahigkeit von Chlorformyloximen", Z. Chem., 8d. 7, Nr. 9, 1967, Seiten 344-345, XPOO1068343.

*Primary Examiner*—Kamal A. Saeed
*Assistant Examiner*—Jason M. Nolan
(74) *Attorney, Agent, or Firm*—Millen, White, Zelano & Branigan, P.C.

(57) ABSTRACT

This invention relates to a process for the production of 4-(17α-alkoxymethyl-17β-substituted-3-oxoestra-4,9-dien-11β-yl)benzaldehyde-(1E)-oxime derivatives of general formula (I)

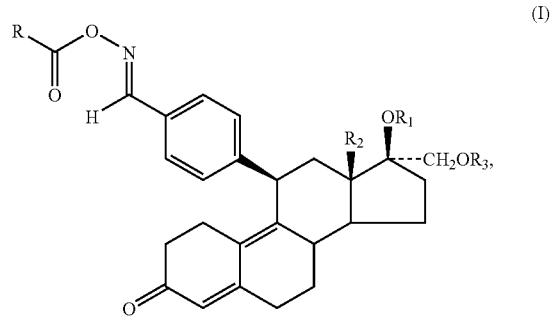

in which R means an amino group, an O—$C_{1-7}$-alkyl- or O-aryl radical, an S—$C_{1-7}$-alkyl- or S-aryl radical, an NH—$C_{1-7}$-alkyl- or NH-aryl radical or an N-di-$C_{1-7}$-alkyl radical, and $R_1$ means a hydrogen atom or a $C_{1-6}$-alkyl radical, which yields the target compounds of formula (I) with high yield and selectivity.

13 Claims, No Drawings

PROCESS FOR THE PRODUCTION OF 4-(17α-ALKOXYMETHYL-17β-SUBSTITUTED 3-OXOESTRA-4,9-DIEN-11β-YL) BENZALDEHYDE-(1E)-OXIME DERIVATIVES

"This application is a 371 of PCT/DE01/04219 filed on Nov. 9, 2001, which claims benefit of German patent application 100 56 677.4, filed Nov. 10, 2000."

The invention relates to a process for the production of 4-(17α-alkoxymethyl-17β-substituted-3-oxoestra-4,9-dien-11β-yl)benzaldehyde-(1E)-oxime derivatives of general formula (I)

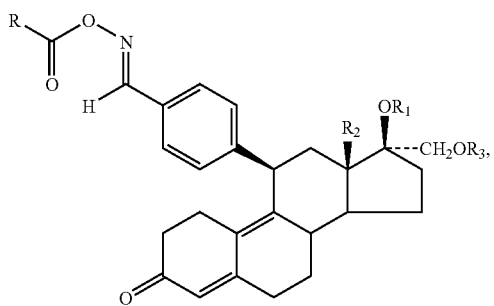

in which R means an amino group, an $O-C_{1-7}$-alkyl or O-aryl radical, an $S-C_{1-7}$-alkyl or S-aryl radical, an $NH-C_{1-7}$-alkyl or NH-aryl radical or an $N$-di-$C_{1-7}$-alkyl radical, $R_1$ means a hydrogen atom or a $C_{1-6}$-alkyl radical, $R_2$ means a $C_{1-4}$-alkyl radical, and $R_3$ means a $C_{1-6}$-alkyl radical.

4-(17α-Alkoxymethyl-17β-substituted-3-oxoestra-4,9-dien-11β-yl)benzaldehyde-(1E)oxime derivatives are known. Substances of this type are described in DE 4332283 A1 (EP 0 648 778 B1) or DE 43 32 284 A1. Because of advantageous antigestagenic action and slight antiglucocorticoidal action, the compounds are of general interest for treating a number of hormone-dependent female diseases, such as, for example, endometriosis.

The existing process for their production starts from an oxime of general formula (II)

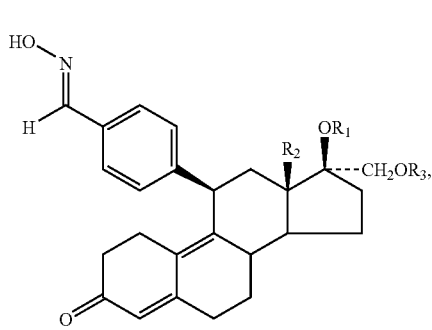

in which $R_1$, $R_2$ and $R_3$ can have the meaning provided above. By reaction with chloroformic acid esters, chloroformic acid thiol esters or isocyanates, the hydroxyl group of the oxime can be esterified or converted into urethanes. The drawback of the process is the formation of nitrites by water elimination and the partial reaction on the free 17β-hydroxyl group with the esterification reagent. The by-products can be separated often with difficulty by chromatography.

The object of this invention is therefore to make available a technically simple and effective process for the production of 4-(17α-alkoxymethyl-17β-substituted-3-oxoestra-4,9-dien-11β-yl)benzaldehyde-(1E)oxime derivatives of formula (I), which on the one hand prevents the attack of the esterification reagent on C-17, and, on the other hand, prevents the elimination of water from the benzaldoxime to the nitrile derivative and thus provides the target compounds of formula (I) with a higher yield and selectivity.

According to the invention, this object is achieved in that benzaldoximes of general formula (II), in which $R_1$, $R_2$ and $R_3$ have the meaning provided above, are reacted with chloroformic acid trichloromethyl ester or phosgene in an inert solvent in the presence of tert-amines, preferably triethylamine, at temperatures of between −35 and +30° C. to form the chloroformic acid derivatives of formula (III)

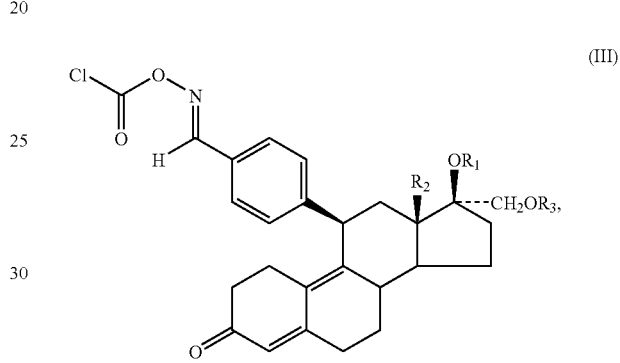

in which $R_1$, $R_2$ and $R_3$ have the meaning provided above, and the chloroformic acid derivatives of formula (III) are reacted with $C_{1-7}$-alkyl- or aryl alcohols, $C_{1-7}$-alkyl- or arylthio alcohols or ammonia or $C_{1-7}$-alkyl- or arylamines or di-$C_{1-7}$-alkylamines to form the 4-(17α-alkoxymethyl-17β-substituted-3-oxoestra-4,9-dien-11β-yl)benzaldehyde-(1E) oxime derivatives of formula (I).

Surprisingly enough, the chloroformic acid trichloromethyl ester neither reacts with a free 17β-hydroxyl group nor is an elimination of water from the benzaldoxime group observed under selected conditions.

To this end, a higher yield is produced in comparison to the process of the prior art. Thus, for example, the phenylurethane compound according to Example 11 can be produced with up to 30% higher yield or the carboxylic acid ester according to Example 1 can be produced with 10% better yield than that that was previously possible with the process according to the prior art. Another advantage of the process according to the invention in comparison to the process of the prior art is its greater variation range. Virtually all alcohols, amines or thiol compounds can be reacted with the chloroformic acid ester (III).

Preferred embodiments of the invention are indicated in the subclaims. Because of additional advantages of the invention, reference is made to the following description and the embodiments.

The reaction is carried out in an inert solvent or in a mixture that consists of inert solvents, whereby aromatic solvents, such as toluene, or ether, such as tetrahydrofuran (THF) or methyl-tert-butyl ether, are preferred.

The reaction is carried out in the presence of a tertiary amine, preferably triethylamine and pyridine, at temperatures of between −35 and +30° C., preferably −35 and +30° C., especially preferably −35° C.

The isolation and purification of the compounds of formula (I) are carried out according to commonly used processes, such as recrystallization or chromatography, for example preparative layer chromatography.

In this invention, "alkyl radical" is defined as a branched or straight-chain alkyl radical or a cyclic alkyl radical that can have one or two heteroatoms in the ring that can be selected from a nitrogen atom, an oxygen atom and a sulfur atom.

As $C_{1-4}$-, $C_{1-6}$- or $C_{1-7}$-alkyl radicals, for example, methyl-, ethyl, n-propyl, i-propyl, n-butyl, i-butyl or tert.-butyl, n-pentyl or i-pentyl, n-hexyl-, 2-pentyl-, 3-pentyl-, 2,3-dimethylbutyl-, n-heptyl-, 2-methylhexyl-, 3-methylhexyl-, 2,2-dimethylpentyl-, 3,3-dimethylpentyl-, 2,3-dimethylpentyl- and 2,2,3-trimethylbutyl groups are mentioned. $R_1$, $R_2$ and $R_3$ preferably mean a $C_{1-3}$-alkyl radical, especially preferably a methyl group.

R means an O—$C_{1-7}$-alkyl-, O-aryl radical, S—$C_{1-7}$-alkyl-, S-aryl radical, NH—$C_{1-7}$-alkyl-, NH-aryl radical or N-Di-$C_{1-7}$-alkyl radical or an amino group.

In the case of R, a cyclic alkyl radical is also preferred that can have one or two heteroatoms in the ring that can be selected from a nitrogen atom, an oxygen atom and a sulfur atom, such as for example, a tetrahydropyranyl group.

The term "aryl" in this application is defined as an aryl, aralkyl or alkylaryl radical with 1 to 10 carbon atoms. Examples of a phenyl radical are a phenyl group, a halophenyl group, a nitrophenyl group or a naphthyl group. Examples of an aralkyl radical are a toluenyl group (methyphenyl group), halotoluenyl group, ethylphenyl group, dimethylphenyl group or a trimethylphenyl group. Examples of an alkylaryl radical are a free or aromatically substituted benzyl group, such as a benzyl group or a halobenzyl group. "Halogen" is defined as a fluorine, chlorine, bromine or iodine atom.

R preferably means an O—$C_{1-4}$-alkyl-, O-aryl radical, S—$C_{1-4}$-alkyl-, S-aryl radical, $NH_2$—NH—$C_{1-4}$-alkyl-, NH-aryl radical or N-di-$C_{1-4}$-alkyl radical, whereby an amino-, methoxy-, ethoxy-, phenoxy-, methylthio-, ethylthio-, NH-methyl-, NH-ethyl-, NH-propyl-, NH-phenyl- or NH-tetrahydropyranyl group is especially preferred.

Most strongly preferred within the scope of the compounds of formula (I) are the following compounds:

4-[17β-Methoxy-17α-(methoxymethyl)-3-oxoestra-4,9-dien-11β-yl]benzaldehyde-1E-[O-(ethyloxy)carbonyl] oxime, 4-[17β-Hydroxy-17α-(methoxymethyl)-3-oxoestra-4,9-dien-11β-yl]benzaldehyde-1E-[O-(ethyloxy)carbonyl] oxime, 4-[17β-Methoxy-17α-(methoxymethyl)-3-oxoestra-4,9-dien-11β-yl]benzaldehyde-1E-[O-(methoxy)carbonyl] oxime, 4-[17β-Hydroxy-17α-(methoxymethyl)-3-oxoestra-4,9-dien-11β-yl]benzaldehyde-1E-[O-(methoxy)carbonyl] oxime, 4-[17β-Methoxy-17α-(methoxymethyl)-3-oxoestra-4,9-dien-11β-yl]benzaldehyde-1E-[O-(ethylamino)carbonyl] oxime, 4-[17β-Hydroxy-17α-(methoxymethyl)-3-oxoestra-4,9-dien-11β-yl]benzaldehyde-1E-[O-(ethylamino)carbonyl] oxime, 4-[17β-Methoxy-17α-(methoxymethyl)-3-oxoestra-4,9-dien-11β-yl]benzaldehyde-1E-[O-(ethylthio)carbonyl] oxime, 4-[17β-Hydroxy-17α-(methoxymethyl)-3-oxoestra-4,9-dien-11β-yl]benzaldehyde-1E-[O-(ethylthio)carbonyl] oxime), 4-[17β-Methoxy-17α-(methoxymethyl)-3-oxoestra-4,9-dien-11β-yl]benzaldehyde-1E-[O-(methylthio)carbonyl] oxime, 4-[17β-Methoxy-17α-(methoxymethyl)-3-oxoestra-4,9-dien-11β-yl]benzaldehyde-1E-[O-(phenyloxy)carbonyl] oxime, 4-[17β-Methoxy-17α-(methoxymethyl)-3-oxoestra-4,9-dien-11β-yl]benzaldehyde-1E-[O-(phenylamino)carbonyl] oxime, 4-[17β-Methoxy-17α-(methoxymethyl)-3-oxoestra-4,9-dien-11β-yl]benzaldehyde-1E-[O-(tetrahydropyranylamino) carbonyl]oxime, 4-[17β-Methoxy-17α-(methoxymethyl)-3-oxoestra-4,9-dien-11β-yl]benzaldehyde-1E-[O-(amino)carbonyl]oxime and 4-[17β-Methoxy-17α-(methoxymethyl)-3-oxoestra-4,9-dien-11β-yl]benzaldehyde-1E-[O-(propylamino)carbonyl] oxime.

The starting compounds of formula (II) are known compounds that can be produced, for example, according to the processes described in DE 4332283 A1 (EP 0 648 778 B1) or DE 43 32 284 A1 or according to the processes that are described in the applications "Process for the Production of 4-(17α-substituted-3-oxoestra-4,9-dien-11β-yl)benzaldehyde-(1E or 1Z)-oximes" and "Process for the Production of 4-(17α-Methyl-substituted 3-Oxoestra-4,9-dien-11β-yl) benzaldehyde-(1E or 1Z)-oximes," which were filed with the German Patent and Trademark Office on the same day as this application by the applicant of this application.

The compounds are well bonded to the gestagen receptor, show a strong antigestagenic activity in the animal experiment and have only slight glucocorticoid receptor binding DE 4332283 A1 (EP 0 648 778 B1) or DE 43 32 284 A1.

The examples below are used for a more detailed description of the invention. General Instructions for the Production of 4-[17β-Methoxy-(17α-(methoxymethyl)-3-oxoestra-4,9-dien-11β-yl]benzaldehyde-1E-(chlorocarbonyl)oxime (III)

900 mg of 4-[17β-substituted-17α-(methoxymethyl)-3-oxoestra-4,9-dien-11β-yl]benzaldehyde-1E-oxime is dissolved in 100 ml of solvent (THF, toluene or methyl-tert.-butyl ether) and mixed at −35° C. with 0.37 ml of chloroformic acid trimethyl ester in 20 ml of solvent. It is stirred for 30 minutes at this temperature, an argon stream is run through for 20 minutes, and (III) is obtained as an intermediate product.

EXAMPLE 1

4-[17β-Methoxy-(17α-(methoxymethyl)-3-oxoestra-4,9-dien-11β-yl]benzaldehyde-1E-[O-(ethoxy)carbonyl]oxime A mixture that consists of 20 ml of ethanol and 20 ml of toluene is added in drops to a solution of 1 g of freshly produced 4-[17β-methoxy-(17α-(methoxymethyl)-3-oxoestra-4,9-dien-11β-yl]benzaldehyde-1E-(chlorocarbonyl) oxime (IIIa) in 100 ml of toluene at −35° C. It is allowed to heat to room temperature, concentrated by evaporation by 50% in a vacuum, water is added, and the phases are separated. The organic phase is washed with water, dried with sodium sulfate and evaporated in a vacuum. The crude product is recrystallized in acetone/hexane.

Melting point 137 to 148° C. (acetone/n-hexane); $\alpha_D$=+204° (CHCl$_3$); $^1$H-NMR: 8.30 (s, 1H, HC=N), 7.63 (d, 2H, J=8.1, H-3'), 7.25 (d, 2H, J=8.1, H-2'), 5.78 (s, 1H, H-4), 4.35 (d, 1H, J=7.2, H-11), 3.56 (d, 2H, J=10.8, CH$_2$O), 3.41 (s, 3H, OCH$_3$), 3.40 (d, 2H, J=10.8, CH$_2$O), 3.25 (s, 3H, OCH$_3$), 1.38 (t, 3H, J=7.0, CH$_2$CH$_3$), 0.51 (s, 3H, H-18).

EXAMPLE 2

4-[17β-Hydroxy-(17α-(methoxymethyl)-3-oxoestra-4,9-dien-11β-yl]benzaldehyde-1E-[O-(ethoxy)carbonyl]oxime 20 ml of ethanol is added in drops to 1 g of 4-[17β-hydroxy-(17α-(methoxymethyl)-3-oxoestra-4,9-dien-11β-yl]benzaldehyde-1E-(chlorocarbonyl)oxime (IIIb) in 100 ml THF at −35° C. It is poured into ice water, extracted with ethyl acetate, washed neutral, dried with sodium sulfate, filtered off and concentrated by evaporation in a vacuum. The crude product is recrystallized in acetone/methyl-tert-butyl ether.

Melting point 161 to 171° C. (acetone/methyl-tert.-butyl ether); $\alpha_D$=+201° (CHCl$_3$); $^1$H-NMR: 8.31 (s, 1H, HC=N), 7.64 (d, 2H, J=8.4, H-3'), 7.25 (d, 2H, J=8.4, H-2'), 5.79 (s, 1H, H-4), 4.38 (d, 1H, J=7.2, H-11), 4.35 (q, 2H, C$\underline{H}_2$CH$_3$), 3.56 (d, 2H, J=9.0, CH$_2$O), 3.41 (s, 3H, OCH$_3$), 3.21 (d, 2H, J=9.0, CH$_2$O), 2.65 (s, 1H, OH), 1.38 (t, 3H, J=7.0, CH$_2$C$\underline{H}_3$), 0.52 (s, 3H, H-18).

EXAMPLE 3

4-[17β-Methoxy-(17α-(methoxymethyl)-3-oxoestra-4,9-dien-11β-yl]benzaldehyde-1E-[O-(methoxy)carbonyl]oxime 15 ml of methanol is added in drops to 1 g of (IIIa) in 100 ml THF at −35° C. It is poured into ice water, extracted with ethyl acetate, washed neutral, the solution is dried with sodium sulfate, filtered off and concentrated by evaporation in a vacuum. The crude product is recrystallized in methyl-tert.-butyl ether.

Melting point 110 to 123° C. (methyl-tert-butyl ether); $\alpha_D$=+171° (CHCl$_3$); $^1$H-NMR: 8.31 (s, 1H, HC=N), 7.63 (d, 2H, J=8.1, H-3'), 7.26 (d, 2H, J=9.0, H-2'), 5.78 (s, 1H, H-4), 4.40 (d, 1H, J=7.2, H-11), 3.92 (s, 3H, OCH$_3$), 3.55 (d, 2H, J=10.5, CH$_2$O), 3.41 (s, 3H, OCH$_3$), 3.40 (d, 2H, J=10.8, CH$_2$O), 3.25 (s, 3H, OCH$_3$), 0.51 (s, 3H, H-18).

EXAMPLE 4

4-[17β-Hydroxy-(17α-(methoxymethyl)-3-oxoestra-4,9-dien-11β-yl]benzaldehyde-1E-[O-(methoxy)carbonyl]oxime 20 ml of methanol is added in drops to 1 g of (IIIb) in 100 ml of THF at −35° C. It is poured into ice water, extracted with ethyl acetate, washed neutral, dried with sodium sulfate, filtered off and concentrated by evaporation in a vacuum. The crude product is purified by preparative layer chromatography on silica gel and recrystallized in acetone/methyl-tert.-butyl ether.

Melting point 158 to 163° C. (acetone/methyl-tert.-butyl ether); $\alpha_D$=+203° (CHCl$_3$); $^1$H-NMR: 8.32 (s, 1H, HC=N), 7.64 (d, 2H, J=8.4, H-3'), 7.24 (d, 2H, J=8.4, H-2'), 5.79 (s, 1H, H-4), 4.41 (d, 1H, J=7.2, H-11), 3.93 (s, 3H, OCH$_3$), 3.56 (d, 2H, J=9.0, CH$_2$O), 3.41 (s, 3H, OCH$_3$), 3.21 (d, 2H, J=9.3, CH$_2$O), 2.66 (s, 1H, OH), 0.51 (s, 3H, H-18).

EXAMPLE 5

4-[17β-Methoxy-(17α-(methoxymethyl)-3-oxoestra-4,9-dien-11β-yl]benzaldehyde-1E-[O-(ethylamino)carbonyl]oxime 30 ml of a solution of 10 ml of ethylamine in 20 ml of THF is added in drops to 1 g of (IIIa) in 100 ml of THF at −35° C. It is poured into ice water, extracted with methyl-tert-butyl ether, washed neutral, dried on sodium sulfate, filtered off and concentrated by evaporation in a vacuum. The crude product is purified by preparative layer chromatography on silica gel and recrystallized in acetone/n-hexane.

Melting point 167 to 171° C. (decomposition, acetone/n-hexane); $\alpha_D$=+221° (CHCl$_3$); $^1$H-NMR: 8.29 (s, 1H, HC=NOR), 7.58 (d, 2H, J=8.4, H-3'), 7.27 (d, 2H, J=8.4, H-2'), 6.27 (t, 1H, J=5.7, NH), 5.79 (s, 1H, H-4), 4.41 (d, 1H, J=7.3, H-11), 3.56 (d, 2H, J=10.6, CH$_2$O), 3.42 (d, 2H, J=10.6, CH$_2$O), 3.41 (s, 3H, OCH$_3$), 3.25 (s, 3H, OCH$_3$), 1.24 (t, 3H, J=7.2, CH$_2$C$\underline{H}_3$), 0.52 (s, 3H, H-18).

EXAMPLE 6

4-[17β-Hydroxy-(17α-(methoxymethyl)-3-oxoestra-4,9-dien-11β-yl]benzaldehyde-1E-[O-(ethylamino)carbonyl]oxime 30 ml of a solution of 10 ml of ethylamine in methyl-tert.-butyl ether is added in drops to 1 g of (IIIb) in 100 ml of methyl-tert.-butyl ether at −35° C. It is poured into ice water, the phases are, separated, washed neutral, the organic phase is dried with sodium sulfate, filtered off and concentrated by evaporation in a vacuum. The crude product is recrystallized in acetone/methyl-tert.-butyl ether.

Melting point 188 to 191° C. (acetone/methyl-tert.-butyl ether); $\alpha_D$=+228° (CHCl$_3$); $^1$H-NMR: 8.30 (s, 1H, HC=NOR), 7.59 (d, 2H, J=8.4, H-3'), 7.28 (d, 2H, J=8.4, H-2'), 6.25 (t, 1H, J=5.2, NH), 5.79 (s, 1H, H-4), 4.42 (d, 1H, J=7.2, H-11), 3.56 (d, 2H, J=9.0, CH$_2$O), 3.42 (s, 3H, OCH$_3$), 3.37 (q, 7.3, NHC$\underline{H}_2$CH$_3$), 3.22 (d, 2H, J=9.0, CH$_2$O), 1.23 (t, 3H, J=7.3, NHCH$_2$C$\underline{H}_3$), 0.53 (s, 3H, H-18).

EXAMPLE 7

4-[17β-Methoxy-(17α-(methoxymethyl)-3-oxoestra-4,9-dien-11β-yl]benzaldehyde-1E-[O-(ethylthio)carbonyl]oxime 20 ml of a solution of 4 ml of ethyl mercaptan in 16 ml of methyl-tert.-butyl ether is added in drops to 1 g of (IIIa) in 100 ml of methyl-tert.-butyl ether at −35° C. It is poured into ice water, the phases are separated, washed neutral, the organic phase is dried with sodium sulfate, filtered off and concentrated by evaporation in a vacuum. The crude product is recrystallized in acetone/n-hexane.

Melting point 148 to 155° C. (acetone/n-hexane); $\alpha_D$=+235° (CHCl$_3$); $^1$H-NMR: 8.31 (s, 1H, HC=NOR), 7.61 (d, 2H, J=8.4, H-3'), 7.27 (d, 2H, J=8.1, H-2'), 5.79 (s, 1H, H-4), 4.41 (d, 1H, J=7.2, H-11), 3.57 (d, 2H, J=10.8, CH$_2$O), 3.42 (d, 2H, J=10.8, CH$_2$O), 3.41 (s, 3H, OCH$_3$), 3.25 (s, 3H, OCH$_3$), 2.95 (q, 2H, J=4.5 and 15, SC$\underline{H}_2$CH$_3$), 1.37 (t, 3H, J=7.0, SCH$_2$C$\underline{H}_3$), 0.52 (s, 3H, H-18).

EXAMPLE 8

4-[17β-Hydroxy-(17α-(methoxymethyl)-3-oxoestra-4,9-dien-11β-yl]benzaldehyde-1E-[O-(ethylthio)carbonyl]oxime 10 ml of a solution of 3 ml of ethyl mercaptan in 7 ml of methyl-tert.-butyl ether is added in drops to 1 g of (IIIb) in 100 ml of methyl-tert.-butyl ether at −35° C. It is poured into ice water, the phases are separated, washed neutral, the organic phase is dried with sodium sulfate, filtered off and concentrated by evaporation in a vacuum. The crude product is purified by preparative layer chromatography on silica gel and recrystallized in dichloromethane/ethyl acetate.

Melting point 176 to 180° C. (dichlormethane/ethyl acetate); $\alpha_D$=+226° (CHCl$_3$); $^1$H-NMR: 8.32 (s, 1H, HC=NOR), 7.62 (d, 2H, J=8.2, H-3'), 7.27 (d, 2H, J=8.2, H-2'), 5.79 (s, 1H, H-4), 4.41 (d, 1H, J=6.7, H-11), 3.56 (d, 2H, J=9.2, CH$_2$O), 3.42 (s, 3H, OCH$_3$), 3.21 (d, 2H, J=9.2, CH$_2$O), 2.95 (q, 2H, SCH$_2$CH$_3$), 1.36 (t, 3H, J=7.2, SCH$_2$CH$_3$), 0.52 (s, 3H, H-18).

EXAMPLE 9

4-[17β-Methoxy-(17α-(methoxymethyl)-3-oxoestra-4,9-dien-11β-yl]benzaldehyde-1E-[O-(methylthio)carbonyl)oxime Methyl mercaptan is introduced into 10 ml of cooled THF for 5 minutes, and this solution is added in drops at −35° C. to 1 g of (IIIa) in 100 ml of THF. After 30 minutes, it is poured into ice water, the phases are separated, the organic phase is washed with water, dried with sodium sulfate, filtered, and concentrated by evaporation in a vacuum. The crude product is recrystallized in acetone/n-hexane.

Melting point 134 to 137° C. (acetone/methyl-tert.-butyl ether); $\alpha_D$=+184° (CHCl$_3$); $^1$H-NMR: 8.32 (s, 1H, HC=NOR), 7.61 (d, 2H, J=7.8, H-3'), 7.29 (d, 2H, J=7.8, H-2'), 5.78 (s, 1H, H-4), 4.41 (d, 1H, J=7.2, H-11), 3.57 (d, 2H, J=10.5, CH$_2$O), 3.42 (d, 2H, J=10.8, CH$_2$O), 3.40 (s, 3H, OCH$_3$), 3.25 (s, 3H, OCH$_3$), 2.40 (s, 3H, SCH$_3$); 0.52 (s, 3H, H-18).

EXAMPLE 10

4-[17β-Hydroxy-(17α-(methoxymethyl)-3-oxoestra-4,9-dien-11β-yl]benzaldehyde-1E-[O-(phenyloxy)carbonyl]oxime The production is carried out analogously to Example 3. The crude product is recrystallized in acetone/n-hexane.

Melting point 101 to 106° C. (decomposition); $\alpha_D$=+179° (CHCl$_3$); $^1$H-NMR: 8.41 (s, 1H, HC=NOR), 7.66 (d, 2H, J=8.4, H-3'), 7.41 (d, 2H, J=7.5, H-2'), 7.25–7.46 (m, 5H, aromatic compound), 5.79 (s, 1H, H-4), 4.41 (d, 1H, J=7.2, H-11), 3.57 (d, 2H, J=10.5, CH$_2$O), 3.42 (d, 2H, J=10.8, CH$_2$O), 3.41 (s, 3H, OCH$_3$), 3.25 (s, 3H, OCH$_3$), 0.52 (s, 3H, H-18).

EXAMPLE 11

4-[17β-Hydroxy-(17α-(methoxymethyl)-3-oxoestra-4,9-dien-11β-yl]benzaldehyde-1E-[O-(phenylamino)carbonyl]oxime The production is carried out analogously to Example 5. The crude product is recrystallized in acetone.

Melting point 241 to 246° C.; $\alpha_D$=+178° (CHCl$_3$); $^1$H-NMR: 8.41 (s, 1H, HC=NOR), 7.56 (d, 2H, J=8.1, H-3'), 7.29 (d, 2H, J=8.4, H-2'), 7.26–7.32 (m, 5H, aromatic compound), 5.79 (s, 1H, H-4), 5.17 (s, 1H, NH), 4.41 (d, 1H, J=6.6, H-11), 3.53 (d, 2H, J=10.8, CH$_2$O), 3.42 (d, 2H, J=10.8, CH$_2$O), 3.41 (s, 3H, OCH$_3$), 3.25 (s, 3H, OCH$_3$), 0.47 (s, 3H, H-18).

EXAMPLE 12

4-[17β-Hydroxy-(17α-(methoxymethyl)-3-oxoestra-4,9-dien-11β-yl]benzaldehyde 1E-[O-(Amino)carbonyl]oxime The production is carried out analogously to Example 5. The crude product is recrystallized in methanol/methyl-tert.-butyl ether.

Melting point 145 to 153° C. (decomposition); $\alpha_D$=+213° (CHCl$_3$); $^1$H-NMR (DMSO): 8.49 (s, 1H, HC=NOR), 7.72 (d, 2H, J=7.8, H-3'), 7.32 (d, 2H, J=7.5, H-2'), 7.11 (s, 2H, NH$_2$), 5.68 (s, 1H, H-4), 4.45 (d, 1H, J=6.9, H-11), 3.57 (d, 2H, J=11.1, CH$_2$O), 3.38 (d, 2H, J=11.1, CH$_2$O), 3.29 (s, 3H, OCH$_3$), 3.12 (s, 3H, OCH$_3$), 0.42 (s, 3H, H-18).

EXAMPLE 13

4-[17β-Hydroxy-(17α-(methoxymethyl)-3-oxoestra-4,9-dien-11β-yl]benzaldehyde-1E-[O-(tetrahydropyranylamino)carbonyl]oxime The production is carried out analogously to Example 5. Colorless foam; $\alpha_D$=+181° (CHCl$_3$); $^1$H-NMR: 8.30 (s, 1H, HC=NOR), 7.57 (d, 2H, J=8.4, H-3'), 7.27 (d, 2H, J=8.1, H-2'), 6.72 (s, 1H, NH), 5.79 (s, 1H, H-4), 5.05 (t, 1H, THP), 4.41 (d, 1H, J=7.2, H-11), 3.56 (d, 2H, J=10.5, CH$_2$O), 3.42 (d, 2H, J=10.5, CH$_2$O), 3.41 (s, 3H, OCH$_3$), 3.25 (s, 3H, OCH$_3$), 0.52 (s, 3H, H-18).

EXAMPLE 14

4-[17β-Hydroxy-(17α-(methoxymethyl)-3-oxoestra-4,9-dien-11β-yl]benzaldehyde-1E-[O-(propylamino)carbonyl]oxime The production is carried out analogously to Example 5. The crude product is recrystallized in acetone/n-hexane.

Melting point 145° C. (decomposition); $\alpha_D$=+222° (CHCl$_3$); $^1$H-NMR (CDCl$_3$): 8.30 (s, 1H, HC=NOR), 7.57 (d, 2H, J=7.8, H-3'), 7.27 (d, 2H, J=7.5, H-2'), 6.28 (t, 1H, NH), 5.79 (s, 1H, H-4), 4.41 (d, 1H, J=6.9, H-11), 3.55 (d, 2H, J=10.5, CH$_2$O), 3.43 (d, 2H, J=10.5, CH$_2$O), 3.41 (s, 3H, OCH$_3$), 3.30 (q, 2H, propyl), 3.25 (s, 3H, OCH$_3$), 0.97 (t, 3H, CH$_3$), 0.52 (s, 3H, H-18).

What is claimed is:

1. A process for preparing a 4-(17α-alkoxymethyl-17β-substituted-3-oxoestra-4,9-dien-11β-yl)benzaldehyde-(1E)-oxime compound of formula (I)

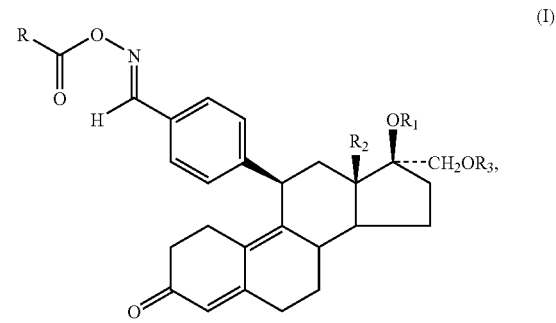

in which
> R means an amino group, an O—$C_{1-7}$-alkyl- or O-aryl radical, an S—$C_{1-7}$-alkyl- or S-aryl radical, an NH—$C_{1-7}$-alkyl- or NH-aryl radical or an N-di-$C_{1-7}$-alkyl radical,
> $R_1$ means a hydrogen atom or a $C_{1-6}$-alkyl radical,
> $R_2$ means a $C_{1-4}$-alkyl radical, and
> $R_3$ means a $C_{1-6}$-alkyl radical,
> comprising reacting a benzadoxime compound of formula (II)

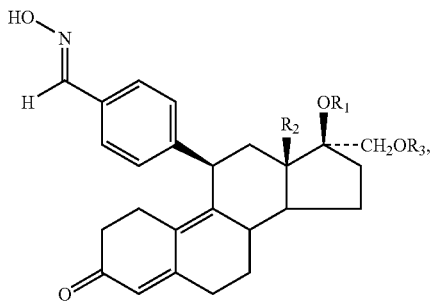

in which
> $R_1$, $R_2$ and $R_3$ have the meanings provided above,
> with chloroformic acid trichloromethyl ester or phosgene in an inert solvent in the presence of a tert-amine compound at a temperature of −35 to +30° C. to form the chloroformic acid compound of formula (III),

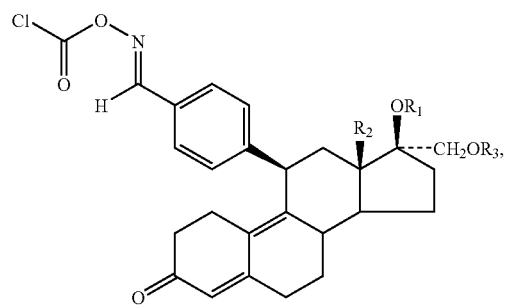

in which
> $R_1$, $R_2$ and $R_3$ have the meanings provided above,
> and reacting the chloroformic acid compound of formula (III) with a $C_{1-7}$-alkyl- or aryl alcohol, $C_{1-7}$-alkyl- or aryl thioalcohol or $C_{1-7}$-alkyl- or arylamine or a di-$C_{1-7}$-alkylamine compound to form a 4-(17α-alkoxymethyl-17β-substituted-3-oxoestra-4,9-dien-11β-yl)benzaldehyde-(1E)oxime compound of formula (I).

2. A process according to claim 1, wherein $R_1$ means a $C_{1-3}$-alkyl radical.

3. A process according to claim 1, wherein $R_2$ means a $C_{1-3}$-alkyl radical.

4. A process according to claim 1, wherein $R_3$ means a $C_{1-3}$-alkyl radical.

5. A process according to claim 1, wherein R means an amino-, methoxy-, ethoxy-, phenoxy-, methylthio-, ethylthio-, NH-methyl-, NH-ethyl-, NH-propyl-, NH-phenyl- or NH-tetrahydropyranyl group.

6. A process according to claim 1, wherein the following compound of formula (I) is prepared:
- 4-[17β-Methoxy-17α-(methoxymethyl)-3-oxoestra-4,9-dien-11β-yl]benzaldehyde-1E-[(O-(ethyloxy)carbonyl]oxime,
- 4-[17β-Hydroxy-17α-(methoxymethyl)-3-oxoestra-4,9-dien-11β-yl]benzaldehyde-1E-[O-(ethyloxy)carbonyl]oxime,
- 4-[17β-Methoxy-17α-(methoxymethyl)-3-oxoestra-4,9-dien-11β-yl]benzaldehyde-1E-[(O-(methoxy)carbonyl]oxime,
- 4-[17β-Hydroxy-17α-(methoxymethyl)-3-oxoestra-4,9-dien-11β-yl]benzaldehyde-1E-[(O-(methoxy)carbonyl]oxime,
- 4-[17β-Methoxy-17α-(methoxymethyl)-3-oxoestra-4,9-dien-11β-yl]benzaldehyde-1E-[(O-(ethylamino)carbonyl]oxime,
- 4-[17β-Hydroxy-17α-(methoxymethyl)-3-oxoestra-4,9-dien-11β-yl]benzaldehyde-1E-[(O-(ethylamino)carbonyl]oxime,
- 4-[17β-Methoxy-17α-(methoxymethyl)-3-oxoestra-4,9-dien-11β-yl]benzaldehyde-1E-[(O-(ethylthio)carbonyl]oxime,
- 4-[17β-Hydroxy-17α-(methoxymethyl)-3-oxoestra-4,9-dien-11β-yl]benzaldehyde-1E-[(O-(ethylthio)carbonyl]oxime,
- 4-[17β-Methoxy-17α-(methoxymethyl)-3-oxoestra-4,9-dien-11β-yl]benzaldehyde-1E-[(O-(methylthio)carbonyl]oxime,
- 4-[17β-Methoxy-17α-(methoxymethyl)-3-oxoestra-4,9-dien-11β-yl]benzaldehyde-1E-[(O-(phenyloxy)carbonyl]oxime,
- 4-[17β-Methoxy-17α-(methoxymethyl)-3-oxoestra-4,9-dien-11β-yl]benzaldehyde-1E-[(O-(tetrahydropyranylamino)carbonyl]oxime,
- 4-[17β-Methoxy-17α-(methoxymethyl)-3-oxoestra-4,9-dien-11β-yl]benzaldehyde-1E-[(O-(amino)carbonyl]oxime, or
- 4-[17β-Methoxy-17α-(methoxymethyl)-3-oxoestra-4,9-dien-11β-yl]benzaldehyde-1E-[(O-(propylamino)carbonyl]oxime.

7. A process according to claim 1, wherein the tert-amine compound is triethylamine.

8. A process according so claim 1, wherein $R_1$ means a methyl group.

9. A process according to claim 1, wherein $R_2$ means a methyl group.

10. A process according go claim 1, wherein $R_3$ means a methyl group.

11. A process according to claim 1, wherein the inert solvent is an aromatic solvent, toluene, ether, tetrahydrofuran or methyl-tert-butyl ether.

12. A process according to claim 1, wherein the benzadoxime compound of formula (II) is reacted with chloroformic acid trichloromethyl ester or phosgene at a temperature −35° C.

13. A process according to claim 1, further comprising isolating and purifying a compound of formula (I) by recrsystalization or chromatography or preparative layer chromatography.

* * * * *

UNITED STATES PATENT AND TRADEMARK OFFICE
CERTIFICATE OF CORRECTION

PATENT NO.        : 7,053,229 B2                                    Page 1 of 1
APPLICATION NO. : 10/416028
DATED             : May 30, 2006
INVENTOR(S)       : Schubert et al.

It is certified that error appears in the above-identified patent and that said Letters Patent is hereby corrected as shown below:

Column 10, line 6, reads "1E-[(O-" should read -- 1E-[O- --
Column 10, line 12, reads "1E-[(O-" should read -- 1E-[O- --
Column 10, line 15, reads "1E-[(O-" should read -- 1E-[O- --
Column 10, line 18, reads "1E-[(O-" should read -- 1E-[O- --
Column 10, line 21, reads "1E-[(O-" should read -- 1E-[O- --
Column 10, line 24, reads "1E-[(O-" should read -- 1E-[O- --
Column 10, line 27, reads "1E-[(O-" should read -- 1E-[O- --
Column 10, line 30, reads "1E-[(O-" should read -- 1E-[O- --
Column 10, line 33, reads "1E-[(O-" should read -- 1E-[O- --
Column 10, line 36, reads "1E-[(O-" should read -- 1E-[O- --
Column 10, line 39, reads "1E-[(O-" should read -- 1E-[O- --
Column 10, line 42, reads "1E-[(O-" should read -- 1E-[O- --
Column 10, line 46, reads "according so claim" should read -- according to claim --
Column 10, line 50, reads "according go claim" should read -- according to claim --
Column 10, line 61, reads "recrsystalization" should read -- recrystallization --
Column 10, insert compound between lines 34 & 35 -- 4-[17b-Methoxy-17a-(methoxymethyl)-3-oxoestra-4,9-dien-11b-yl]benzaldehyde-1E-[O-(phenylamino)carbonyl]oxime, --

Signed and Sealed this

Twenty-sixth Day of December, 2006

JON W. DUDAS
*Director of the United States Patent and Trademark Office*